United States Patent [19]

Mazur et al.

[11] 3,966,777

[45] June 29, 1976

[54] PROCESS FOR THE PRODUCTION OF 1α-HYDROXY PROVITAMIN $D_3$ AND 1α-HYDROXY VITAMIN $D_3$

[75] Inventors: Yehuda Mazur, Tel-Aviv; Dalia Freeman, Rishon Lezion; Aureliu J. Acher, Ramat-Gan, all of Israel

[73] Assignee: Yeda Research & Development Co. Ltd., Rehovot, Israel

[22] Filed: Oct. 15, 1975

[21] Appl. No.: 622,647

[30] Foreign Application Priority Data

Oct. 22, 1974 Israel.................................... 45897

[52] U.S. Cl.................... 260/397.2; 260/239.55 R; 424/236
[51] Int. Cl.²............................................ C07J 9/00
[58] Field of Search................................ 260/397.2

[56] References Cited
UNITED STATES PATENTS

| | | | |
|---|---|---|---|
| 3,739,001 | 6/1973 | DeLuca | 260/397.2 |
| 3,929,770 | 12/1975 | Ishikawa et al. | 260/397.2 |

Primary Examiner—Elbert L. Roberts
Attorney, Agent, or Firm—Browdy and Neimark

[57] ABSTRACT

A process for the production of 1α-hydroxy provitamin $D_3$ which comprises treating 1α, 2α-epoxy-cholesta-4,6-diene-3-one at a low temperature with liquid ammonia; with ammonium chloride and with lithium metal to produce 1α,3β-dihydroxycholest-6-ene, converting this to the corresponding 1α,3β-di(lower alkanoyl) derivative, reacting the latter with bromine to give 1α,3β-di(lower alkanoyloxy) 6β,7α-dibromocholestane, which is dehydrobrominated to give 1α,3β-di(lower alkanoyloxy)-cholesta-5,7-diene, which is converted to the desired provitamin. The 1α,3β-di(lower alkanoyloxy)cholest-6-ene can be oxidized to the corresponding 5-ene-7-one, which is converted to the 7-p-toluenesulfonyl hydrazone derivative, which is converted to the 1α-hydroxy provitamin $D_3$ di(lower alkanoyloxy) derivative or to the 1α-hydroxy provitamin $D_3$. Novel compounds are 1α,3β-dihydroxy-cholest-6-ene, its di(lower alkanoyloxy) derivative; 1α,3β-di(lower alkanoyloxy)-6β,7α-dibromocholestane; 1α,3β-diacetoxycholest-5-ene-7-one and the corresponding 7-p-toluenesulfonylhydrazone derivative.

16 Claims, No Drawings

PROCESS FOR THE PRODUCTION OF 1α-HYDROXY PROVITAMIN D₃ AND 1α-HYDROXY VITAMIN D₃

FIELD OF THE INVENTION

The present invention relates to a novel process for the production of 1α-hydroxy vitamin $D_3$ and also for the production of the precursor thereof, 1α-hydroxy provitamin $D_3$. The present invention also relates to novel intermediates, which are of value in the synthesis of the above vitamin and provitamin and which are also valuable intermediates in organic chemistry in general, and in the production of derivatives of cholestane, in particular. 1α-hydroxy provitamin $D_3$ can be converted to vitamin $D_3$ in a manner similar to the conversion of provitamin $D_3$ to vitamin $D_3$, i.e. by irradiation with ultraviolet light, see Windaus et al. Ann 533, 118 (1938).

BACKGROUND OF THE INVENTION

It has been reported that 1α-hydroxy-vitamin $D_3$ has a physiological activity, mainly in the transport of calcium to the bones; Omdahl et al., Physiol. Rev. 53. 327 (1973).

It is known to convert cholesterol to 1α,2α-epoxycholesta-4,6-dien-3-one (I) and to treat this latter with lithium metal in liquid ammonia, resulting in the production of 1α,3β-dihydroxycholest-5-ene (V), which is also a precursor of 1α-hydroxy-vitamin $D_3$; Barton et al., J.A.C.S. 95, 2748 (1973).

The process of the present invention starts with the same epoxy derivative (I), and is treated with lithium and ammonium chloride in liquid ammonia, but under different conditions of reaction, so as to result mainly in the novel 1α,3β-dihydrocholest-6-ene (II), which is converted to the corresponding 1α,3β-dialkanoyloxy-cholest-6-ene (III); the latter is brominated to yield 1α,3β-dialkanoyloxy-6β,7α-dibromocholestane (IV) which is reacted with an anhydrous base to give the di(alkanoyloxy) derivative of 1α-hydroxy provitamin $D_3$, which can be converted to 1α-hydroxy provitamin $D_3$ or 1α-hydroxy vitamin $D_3$.

According to another route, the process of the invention comprises oxidizing compound III to the corresponding 7-keto derivatve VII, which is reacted with toluene sulfonyl hydrazone to yield the corresponding 7-toluene sulfonyl hydrazone (VIII) which upon heating with lithium hydride gives the desired 1α-hydroxy provitamin $D_3$.

The novel compounds of the formulas II and III are;

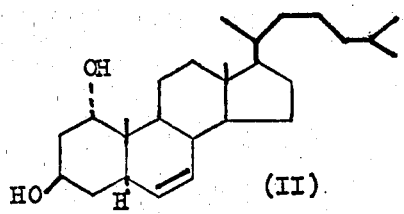

(II)

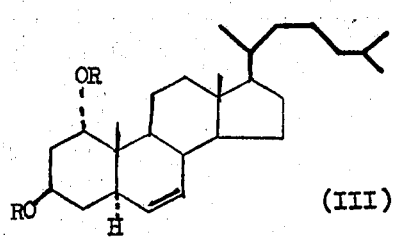

(III)

those of formulas IV and VII are;

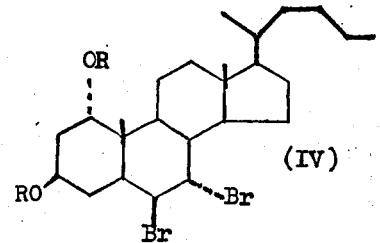

(IV)

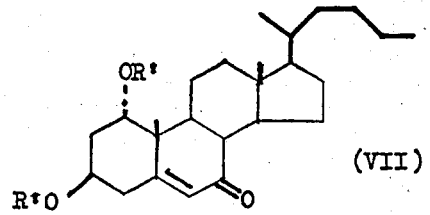

(VII)

while those of formulas I and VI are:

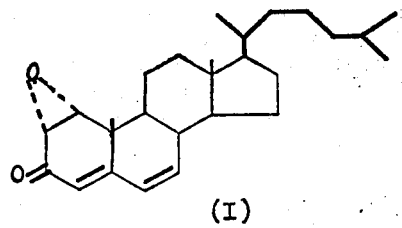

(I)

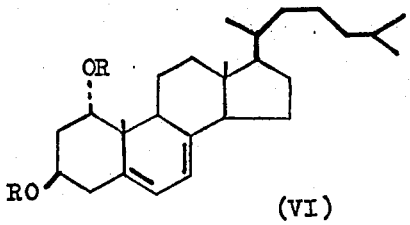

(VI)

wherein R designates lower alkanoyl.

The process of the present invention comprises treating 1α,2α-epoxy-cholesta-4,6-dien-3-one (I), dissolved in a suitable solvent at a low temperature (of about −30°C) with liquid ammonia, followed with a repeated treatment with ammonium chloride followed by lithium metal. Suitable solvents are ethers, such as tetrahydrofuran. Advantageously there is used an excess of ammonium chloride, and this is followed by an excess of lithium. This is repeated a number of times, usually between 4 and 7 times. The main product of this process step is the production of 1α,3β-dihydroxycholest-6-ene (II) which is obtained in a yield of about 50 percent. Byproducts are cholesterol and the known 1α,3β-dihydroxycholest-5-ene.

1α,3β-dihydroxycholest-6-ene is converted to the corresponding 1α,3β-di(lower alkanoyl)-derivative III, which is reacted with bromine to give the dibromo-derivative IV, which latter is dehydrobrominated by treatment with a suitable base, such as an alkylated pyridine, dimethyl formamide, hexamethylphosphoramide or the like. The preferred embodiment comprises heating the reactant IV with hexamethylphosphoramide for a number of hours at a temperature of about 100°C to about 140°C, in the presence of a small quantity of tetraalkyl ammonium salts of a dialkyl phosphate or with similar salts of an alkyl phosphonate. The latter results in a yield of about 50 percent of the desired 1α-hydroxy provitamin $D_3$. The conversion of the latter to 1α-hydroxy vitamin $D_3$ has been described previously.

A modification of the process of the present invention takes a different route, starting with compound III. The 1α,3β-(di-lower alkanoyl)cholest-6-ene in a solvent like tert-butanol is treated with mercuric bromide and sodium acetate and irradiated at room temperature at a wavelength of about 254 nm, during about 5 hours. After filtration and extraction with a solvent like hexane, there is obtained 1α,3β-dihydroxycholest-5-en-7-one-di(lower alkanoyl) derivative VII. The latter is dissolved in a solvent like methanol, treated with p-toluenesulfonylhydrazine and heated during about 5 hours under an inert gas, such as nitrogen. The solvents were removed under reduced pressure and the residue was dissolved in methylene chloride and subjected to chromatography on alumina to give the p-toluene-sulfonylhydrazone derivative VIII, which was dissolved in dry toluene and treated with lithium hydride. After refluxing under nitrogen the reaction mixture is cooled, filtered, and the precipitate was washed with ether. The combined organic fractions were washed with dilute aqueous sulfuric acid, with water, and evaporated, resulting in 1α,3β-(di-lower alkanoyl)-cholest-5,7-diene.

The preferred intermediate if the formula III is the 1α,3β-diacetate.

Due to its physiological properties, 1α-hydroxy provitamin $D_3$ and 1α-hydroxy vitamin $D_3$, obtained from the provitamin are valuable additives to foodstuffs for human and for animal use. They can be used in vitamin preparations of various kinds, and are especially useful as ingredients in multivitamins.

DESCRIPTION OF THE PREFERRED EMBODIMENT

The invention is described by way of example only in the following. The examples are to be construed in a non-limitative manner.

EXAMPLE 1

To a solution of 6 g of 1α,2α-epoxy-cholesta-4,6-diene-3-one, (I) dissolved in 340 ml of dry, freshly distilled tetrahydrofuran was added at −30°C 480 ml liquid ammonia. The solution was stirred and at this same temperatures there was added a quantity of 4.3 g dry ammonium chloride, followed by 0.5 g lithium metal which was added in the form of small granules. After a period of time of about 5 minutes the blue colour of the solution faded, and further 4 g ammonium chloride were added, followed by 0.5 g of lithium metal. This procedure was repeated four times. After the last addition of lithium, the reaction mixture was maintained for 2 hours at −25°C and after this ammonium chloride was added until disappearance of the blue colour. The reaction mixture was left to stand at room temperature and extracted with ether. The residue was subjected to chromatography on silica to give 1 g of cholesterol, M.P. 145°–146°C; 1.2 g of 1α,3β-dihydroxycholest-5-ene (V), of M.P. 156°–157°C and 3.5 g of 1α,3β-dihydroxycholest-6-ene (II), M.P. 143°–145°C, $[\alpha]_D = -65°$.

EXAMPLE 2

A quantity of 10 g of 1α,3β-dihydroxycholest-6-ene was dissolved in 100 ml pyridine and treated with 90 ml acetic anhydride. The solution was heated to 80°C and maintained at this temperature for 24 hours. The product was extracted with ether to give 8 g of 1α,3β-diacetoxycholest-6-ene, M.P. = 116°–118°C, $[\alpha]_D = -74°$ (III)

EXAMPLE 3

A solution of 10 g of 1α,3β-diacetoxycholest-6-ene (III) in 50 ml methylene chloride was cooled with ice water and there was added dropwise 16 ml of a 17 percent weight per volume solution of bromine in methylene chloride. The yellow solution was stirred for 10 minutes at room temperature, extracted after this with ether and washed with a solution of potassium carbonate. There was obtained a crop of 9.5 g of 1α,3β-diacetoxy-6β,7α-dibromocholestane, (IV) which was recrystallized from methanol. M.P. 155°–156°C, $[\alpha]_D = -25°$.

EXAMPLE 4

A solution of 0.5 g of the dibromide (IV) of Example 3 in 50 ml hexamethylphosphoramide was treated with 0.5 g triethyl methylammonium dimethylphosphate (prepared by heating triethylamine with trimethylphosphate), and heated at 135°C for 3 hours under nitrogen. The resulting product was isolated from hexane and subjected to chromatography on silica impregnated with silver nitrate. Elution was effected with hexane-benzene mixtures (1:3) resulted in 0.25 g of 1α,3β-diacetoxycholesta-5,7-diene (VI), M.P. 113°–114°C, $[\alpha]_D = -30°$. $\lambda_{max}$ 262,271, 282,294 nm, ($\epsilon$8300, 12000, 13000, and 7500) in cyclohexane.

EXAMPLE 5

A solution of 0.3 g of 1α,3β-diacetoxycholest-6-ene in 30 ml tert-butanol was treated with 0.3 g mercuric bromide and 0.03 g sodium acetate. The stirred mixture was irradiated with light of 254 nm wavelength at room temperature during 5 hours. After filtration and extraction with 300 ml hexane, there was obtained a quantity of 0.21 g of 1α,3β-diacetoxycholest-5-en-7-one. M.P. = 121°–122°C.

A solution of 0.2 g of 1α,3β-diacetoxy-cholest-5-en-7-one in 10 ml methanol was treated with 0.2 g p-toluenesulfonyl hydrazide and heated (refluxed) during 5 hours under nitrogen. The solution was evaporated under reduced pressure and the thus obtained residue was dissolved in 3 ml methylene chloride and subjected to chromatography on a column of alumina to yield 0.18 g of the p-toluenesulfonyl-hydrazone derivative. This was dissolved in 15 ml of dry toluene and reacted with 0.2 g of lithium hydride. The reaction mixture was refluxed overnight under an atmosphere of nitrogen. After cooling, the reaction mixture was filtered and the precipitate was washed with 20 ml ether. The combined organic fraction was washed with dilute sulfuric acid and with water. After evaporation, there was obtained 0.12 g of 1α,3β-diacetoxy cholest -5,7-diene, M.P. = 113°–114°C, $[\alpha]_D = -30°$, identical with an authentic sample.

The products of all the examples were analyzed. Elemental analysis, mass spectra and N.M.R. measurements confirmed the structure and composition of the products.

The $1\alpha,3\beta$-di(lower alkanoyloxy)cholest-5,7-diene can be converted by conventional means to the $1\alpha$-hydroxy provitamin $D_3$ or directly to $1\alpha$-hydroxy vitamin $D_3$.

Following are structural formulae for each of the eight compounds referred to herein, I–VIII, showing the various steps in the process described above.

lithium metal to result in $1\alpha,3\beta$-dihydroxycholest-6-ene, converting this to the corresponding $1\alpha,3\beta$-di(lower alkanoyloxy)-derivative, reacting the latter with bromine to give $1\alpha,3\beta$-di-lower alkanoyloxy $6\beta,7\alpha$-dibromocholestane, which latter is dehydrobrominated with a base to give $1\alpha,3\beta$-di(lower alkanoyloxy)-cholesta-5,7-diene which is converted to the $1\alpha$-hydroxy provitamin $D_3$.

2. A process according to claim 1, wherein the treatment with ammonium chloride and with lithium metal is repeated a number of times.

3. A process according to claim 1, wherein $1\alpha,3\beta$-dihydroxycholest-6-ene is converted to the corresponding $1\alpha,3\beta$-diacetoxy derivative by treatment with acetic anhydride in pyridine.

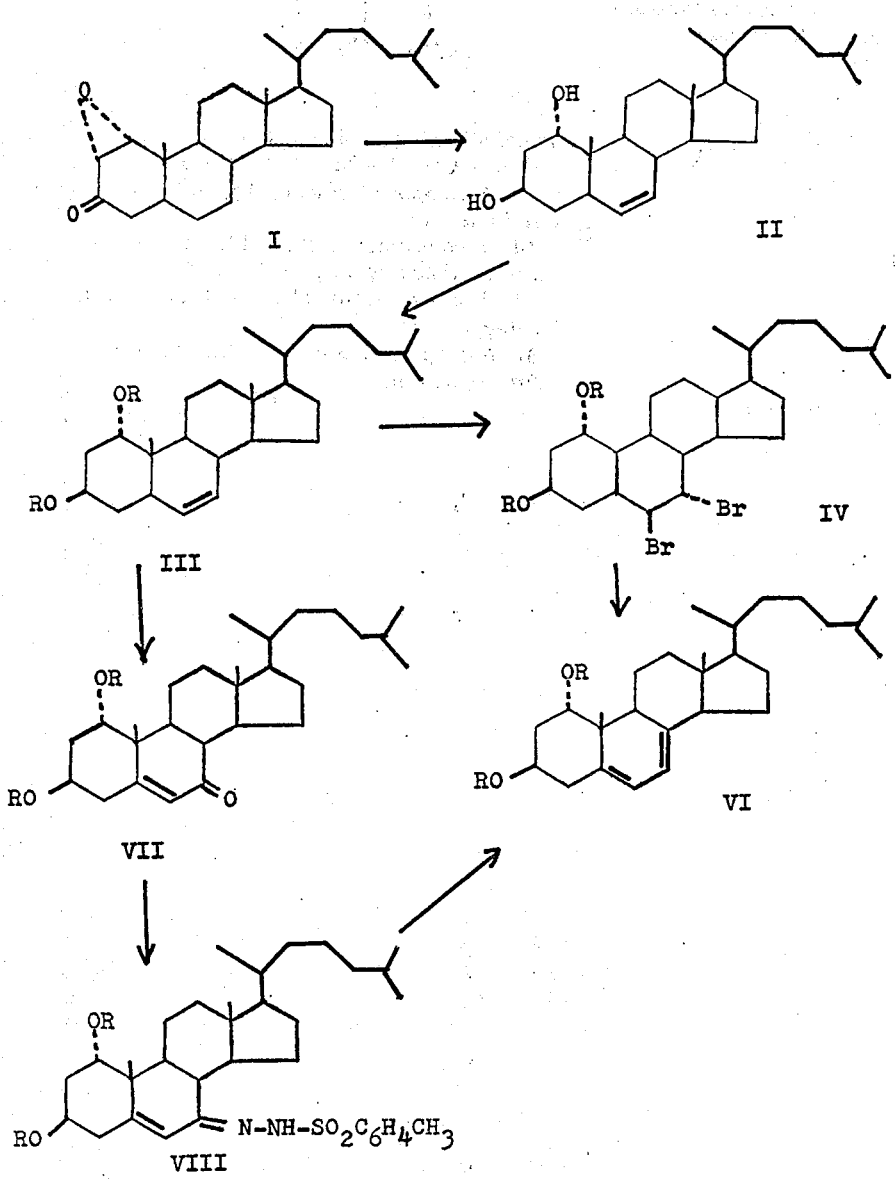

We claim:

1. Process for the production of $1\alpha$-hydroxy provitamin $D_3$ ($1\alpha$-hydroxy-7-dehydrocholesterol) which comprises treating $1\alpha,2\alpha$-epoxy-cholesta-4,6-dien-3-one, dissolved in a solvent, at a low temperature with liquid ammonia, with ammonium chloride and with 4. A process according to claim 1, wherein the dehydrobromination is effected by treatment of a base selected from alkylated pyridines, dialkyl formamide, hexamethylformamide.

5. A process according to claim 4, wherein the dehydrobromination is effected with hexamethylphosphoramide in the presence of a tetraalkyl ammonium salt of a dialkyl phosphate at a temperature of from 100° to 140°C.

6. A process for the production of 1α-hydroxy provitamin $D_3$ which comprises converting 1α,3β-di(lower alkanoyloxy)cholest-6-ene to 1α,3β-dihydroxy-cholest-5-ene-7-one by treatment with mercuric bromide and sodium acetate and irradiation at a wavelength of about 254 nm, dissolving the latter in a solvent, treating the solution with p-toluene sulfonylhydrazine to give the corresponding 7-p-toluene sulfonylhydrazone derivative which is treated with lithium hydride to give 1α,3β-di(lower alkanoyloxy)cholest-5,7-diene.

7. A process according to claim 6, wherein the starting compound is 1α,3β-diacetoxy-cholest-6-ene.

8. A compound of the formula

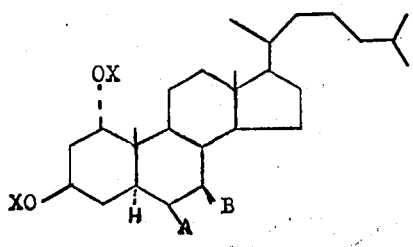

wherein X is hydrogen or lower alkanoyl,

A—B is a 6(7) double bond or A is —Br and B is —Br.

9. A compound of claim 8, 1α,3β-dihydroxy-cholest-6-ene.

10. A compound of claim 8, 1α,3β-di(lower alkanoyloxy)-cholest-6-ene.

11. A compound of claim 8, 1α,3β-di(lower alkanoyloxy)6β,7α-dibromocholestane..

12. A compound of the formula

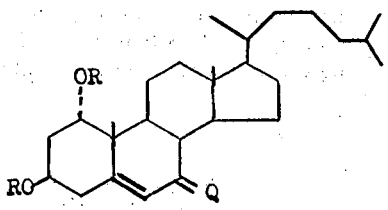

wherein R is lower-alkanoyl and
Q is =O or =N—NH—SO$_2$—C$_6$H$_4$CH$_3$.

13. A compound of claim 12, 1α,3β-diacetoxy-cholest-5-ene-7-one.

14. A compound of claim 12, 1α,3β-diacetoxy,7-p-toluenesulfonyl hydrazone cholest-5-one.

15. A compound of claim 8, 1α,3β-diacetoxy-cholest-6-ene.

16. A compound of claim 8, 1α,3β-diacetoxy-6β,7α-dibromocholestane.

* * * * *